(12) United States Patent
Pettit et al.

(10) Patent No.: US 7,709,643 B2
(45) Date of Patent: May 4, 2010

(54) SYNTHESIS OF SODIUM NARCISTATIN AND RELATED COMPOUNDS

(75) Inventors: George R. Pettit, Paradise Valley, AZ (US); Noeleen Melody, Mesa, AZ (US)

(73) Assignee: Arizona Board of Regents, a body corporate of the State of Arizona, Acting for and on Behalf of the Arizona State University, Scottsdale, AZ (US)

( * ) Notice: Subject to any disclaimer, the term of this patent is extended or adjusted under 35 U.S.C. 154(b) by 0 days.

(21) Appl. No.: 11/813,657

(22) PCT Filed: Jan. 17, 2006

(86) PCT No.: PCT/US2006/001658

§ 371 (c)(1),
(2), (4) Date: Jan. 21, 2009

(87) PCT Pub. No.: WO2006/076726

PCT Pub. Date: Jul. 20, 2006

(65) Prior Publication Data

US 2009/0131672 A1    May 21, 2009

Related U.S. Application Data

(60) Provisional application No. 60/644,397, filed on Jan. 14, 2005.

(51) Int. Cl.
*C07D 491/12*  (2006.01)
*C07D 491/056*  (2006.01)

(52) U.S. Cl. ............... 546/23; 546/65; 546/48

(58) Field of Classification Search ............ 546/23, 546/48, 65
See application file for complete search history.

(56) References Cited

FOREIGN PATENT DOCUMENTS

WO    WO 2004/052298    6/2004

OTHER PUBLICATIONS

International Search Report for PCT/US2006/001658 dated Jun. 16, 2006.
Written Opinion of the International Search Authority for PCT/US2006/001658 dated Jun. 16, 2006.
Pettit et al., "Antineoplastic Agents. 511. Phosphorylation of Phenpanstatin and Pancratistatin", *J. Nat. Prod.*, 67:322-327 (2004).
European Search Report for EP 06 71 8694 dated Jan. 9, 2008.
Pettit et al., "Antineoplastic Agents 500. Narcistatin", *J. Nat. Prod.*, 66(1):92-96 (2003).

*Primary Examiner*—Charanjit S Aulakh
(74) *Attorney, Agent, or Firm*—McAndrews Held & Malloy Ltd.

(57) ABSTRACT

The present invention involves use of the compounds narciclasine (2a) and 7-deoxy-narciclasine (2c), which are obtained via isolation from the medicinal plant species *Narcissus* (Amaryllidaceae), as precursors in a novel synthesis method in which each of these compounds are selectively hydrogenated to produce trans-dihydronarciclasine (1a) and 7-deoxy-trans-dihydronarciclasine (1c). Also described herein is a novel synthesis method for producing sodium narcistatin (11) from narciclasine (2a). Further described herein are certain novel 3,4-cyclic phosphate prodrugs, including sodium-7-deoxynarcistatin (8), sodium-7-deoxy-transdihydronarcistatin (9), and sodium transdihydronarcistatin (10).

6 Claims, 5 Drawing Sheets

1a, $R_1$ = OH, $R_2$ = $R_3$ = $R_4$ = H; *trans*-dihydronarciclasine
1b, $R_1$ = OAc, $R_2$ = $R_3$ = $R_4$ = Ac
1c, $R_1$ = $R_2$ = $R_3$ = $R_4$ = H; 7-deoxy-*trans*-dihydronarciclasine
1d, $R_1$ = H, $R_2$ = Si(CH$_3$)$_2$C(CH$_3$)$_3$, $R_3$,$R_4$ = C(CH$_3$)$_2$
1e, $R_1$ = $R_2$ = H, $R_3$,$R_4$ = C(CH$_3$)$_2$

2a, $R_1$ = OH, $R_2$ = $R_3$ = $R_4$ = H;
narciclasine
2b, $R_1$ = OAc, $R_2$ = $R_3$ = $R_4$ = Ac
2c, $R_1$ = $R_2$ = $R_3$ = $R_4$ = H;
7-deoxynarciclasine
2d, $R_1$ = OH, $R_2$ = H, $R_3$,$R_4$ = C(CH$_3$)$_2$
2e, $R_1$ = $R_2$ = H, $R_3$,$R_4$ = C(CH$_3$)$_2$
2f, $R_1$ = H, $R_2$ = Si(CH$_3$)$_2$C(CH$_3$)$_3$, $R_3$,$R_4$ = C(CH$_3$)$_2$

3a, $R_1$ = OH, $R_2$ = $R_3$ = $R_4$ = H;
*cis*-dihydronarciclasine
3b, $R_1$ = OAc, $R_2$ = $R_3$ = $R_4$ = Ac
3c, $R_1$ = H, $R_2$ = Si(CH$_3$)$_2$C(CH$_3$)$_3$, $R_3$,$R_4$ = C(CH$_3$)$_2$

4a, $R_1$ = OH, $R_2$ = $R_3$ = $R_4$ = H;
*iso*-narciclasine
4b, $R_1$ = OAc, $R_2$ = $R_3$ = $R_4$ = Ac
4c, $R_1$ = H, $R_2$ = Si(CH$_3$)$_2$C(CH$_3$)$_3$, $R_3$,$R_4$ = C(CH$_3$)$_2$

5, (+)-Pancratistatin

6, Wilkinson's catalyst

7, Crabtree's catalyst

Scheme 1

Figure 2

Scheme 2:

SYNTHESIS OF SODIUM NARCISTATIN AND RELATED COMPOUNDS

CROSS-REFERENCE TO RELATED APPLICATIONS

This application is the U.S. national stage of PCT/US2006/001658 filed on Jan. 17, 2006, which is based on and claims the priority to U.S. Provisional Patent Application No. 60/644,397 filed on Jan. 14, 2005, the disclosure of which is incorporated herein in its entirety.

STATEMENT OF FEDERALLY SPONSORED RESEARCH

Financial assistance for this invention was provided by the United States Government, Division of Cancer Treatment and Diagnosis, National Cancer Institute, Department of Health and Human Services Outstanding Investigator Grant Numbers CA-44344-01A1-01-12; CA 44344-01-12 and CA 90441-01-03; the Arizona Disease Control Research Commission; and private contributions. Thus, the United States Government has certain rights in this invention.

FIELD OF THE INVENTION

The present invention relates certain compounds, and methods for synthesis of certain compounds, wherein the compounds have shown anti-neoplastic activity against cancerous cell lines, and therefore are anticipated to be useful in the treatment of various forms of cancer in animals and humans.

SUMMARY OF THE INVENTION

The present invention involves use of the compounds narciclasine (2a) and 7-deoxy-narciclasine (2c), which are obtained via isolation from the medicinal plant species *Narcissus* (Amaryllidaceae), as precursors in a novel synthesis method in which each of these compounds are selectively hydrogenated to produce trans-dihydronarciclasine (1a) and 7-deoxy-trans-dihydronarciclasine (1c). Also described herein is a novel synthesis method for producing sodium narcistatin (11) from narciclasine (2a). Further described herein are certain novel 3,4-cyclic phosphate prodrugs, including sodium-7-deoxynarcistatin (8), sodium-7-deoxy-transdihydronarcistatin (9), and sodium transdihydronarcistatin (10).

The present invention involves use of the compounds narciclasine (2a) and 7-deoxy-narciclasine (2c) which are obtained via isolation from certain *Narcissus* (Amaryllidaceae) as precursors in a novel and unobvious process by which each of these compounds may be selectively hydrogenated to produce trans-dihydronarciclasine (1a) and 7-deoxytrans-dihydronarciclasine (1c).

DETAILED DESCRIPTION OF THE INVENTION

Materials and Methods

Figure 1:
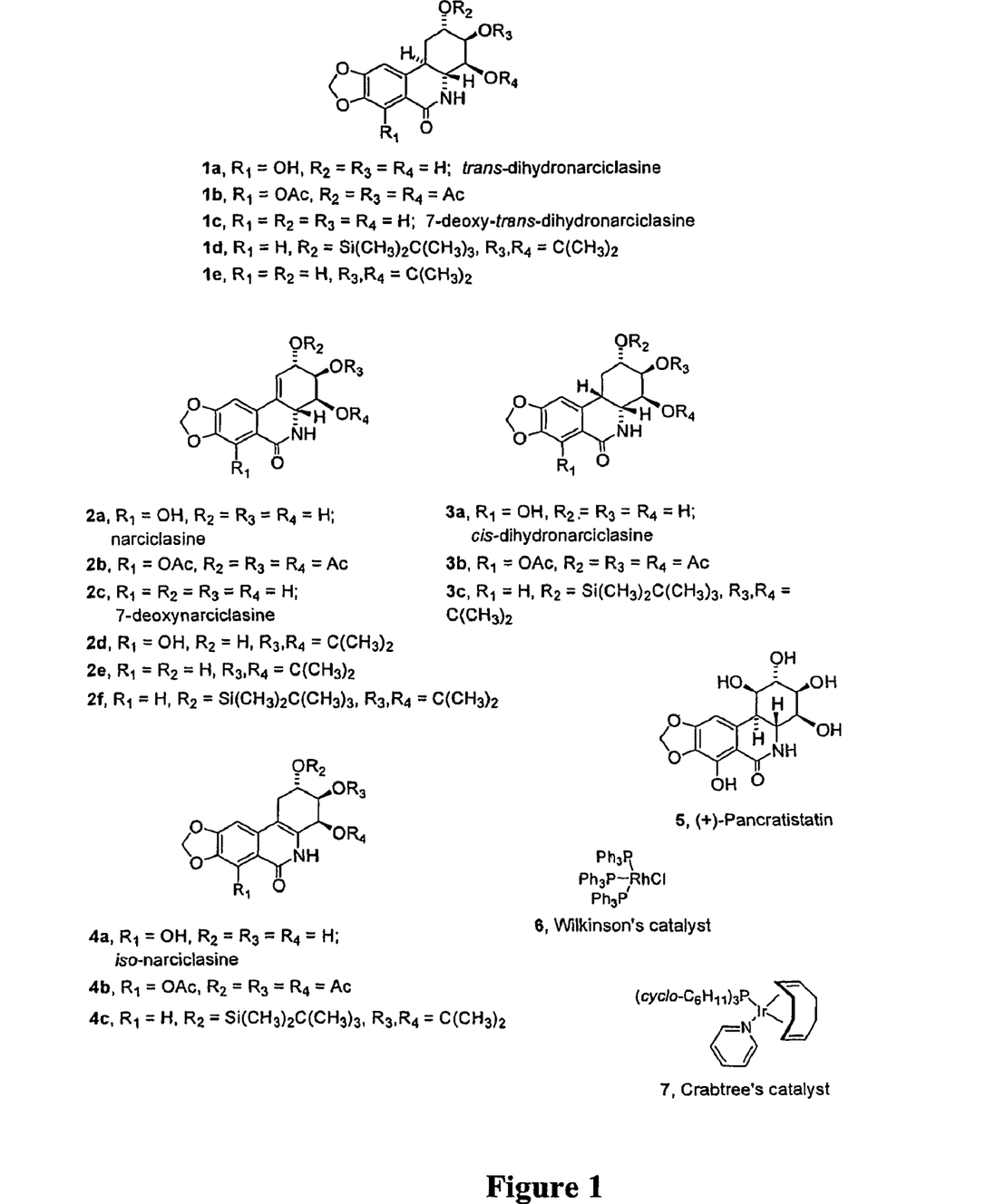
FIG. 1 shows structural formulas for the compounds described herein
Figure 2:
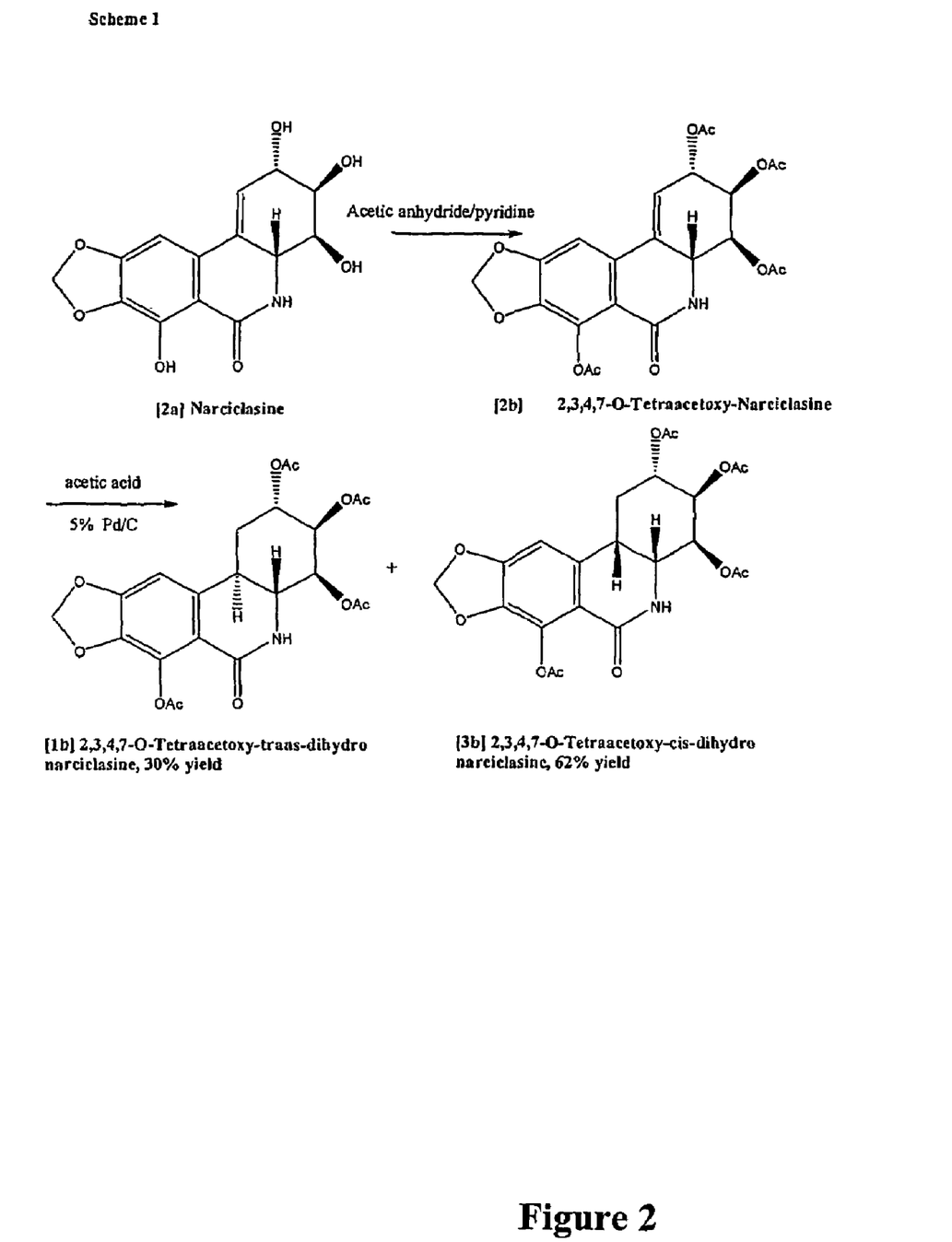
FIG. 2 shows reaction schemes for synthesizing some of the compounds of the present invention.

The isolation of new compounds from substances found in nature, such as plants, and the creation of derivatives of these compounds, is an active area of research for compounds having pharmaceutical utility. Described herein are methods for the synthesis of, and for the use of such "natural" compounds in the synthesis of other compounds, many of which show promise as anti-neoplastic drugs.

From a 1982 collection (bulbs) of the Chinese medicinal plant *Zephyranthes candida* (Amaryllidaceae) was isolated the strong ($ED_{50}$ 0.0032 µg/ml) P388 lymphocytic leukemia cell growth inhibitor trans-dihydronarciclasine (1a). (Pettit G. R., et al., Antineoplastic 162. *Zephyranthes candida*. J. Nat. Prod. 53:176-178; 1990.) The structure was established by detailed spectral analyses of its peracetate derivative (1b) and confirmed by comparison with the product from catalytic hydrogenation of narciclasine (2a). (Mondon, A., et al., Zur Kenntnis des Narciclasins. Chem. Ber. 108:445-463; 1975.) Hydrogenation afforded as the major product the expected cis-dihydronarciclasine (3a), accompanied by the trans isomer (1a) and iso-narciclasine (4a). More recently, trans-dihydronarciclasine (1a) was found to exhibit strong cancer cell growth inhibition (mean panel $GI_{50}$ 12.6 nM) against the U.S. National Cancer Institute (NCI) panel of cancer cell lines, whereas its cis isomer (3a) was only very weakly active (mean panel $GI_{50}$ 3800 nM). (Pettit, G. R., et al., Antineoplastic agents 256. Cell growth inhibitory isocarbostyrils from *Hymenocallis*. J. Nat. Prod. 56: 1682-1687; 1993.) Importantly, the trans isomer (1a) gave an active Compare correlation coefficient of 0.92 in respect to (+)-pancratistatin (5) equals 1.00. (Pettit, G. R., et al., Antineoplastic agents 256. Cell growth inhibitory isocarbostyrils from *Hymenocallis*. J. Nat. Prod. 56: 1682-1687; 1993.) The trans isomer (1a) also showed strong activity against a range of RNA viruses while the synthetic cis isomer (3a) was completely inactive. (Gabrielsen, B., et al., Antiviral (RNA) activity of selected Amaryllidaceae isoquinoline constituents and synthesis of related substances. J. Nat. Prod. 55:1569-1581; 1992.)

Narciclasine (2a) was isolated from the bulbs of *Narcissus imcomparabilus*, and 7-deoxynarciclasine (2c) and 7-deoxytransdihydronarciclasine (1c) were isolated from the bulbs of *Hymenocallis littoralis* grown by the ASU-CRI research group in Tempe, Ariz., now part of the Arizona Biodesign Institute. (Piozzi, F., et al., Narciclasine and Narciprimine. Tetrahedron. 24:1119-1131; 1968.), (Pettit, G. R., et al., Antineoplastic agents 256. Cell growth inhibitory isocarbostyrils from *Hymenocallis*. J. Nat. Prod. 56: 1682-1687; 1993.). All solvents were redistilled, and reagents were purchased from Lancaster, Sigma-Aldrich Co. and Aeros Chemical Co. Reaction progress was ascertained by thin-layer chromatography using Analtech silica gel GHLF Uniplates visualized under long- and short-wave UV irradiation and developed in an ethanolic solution of phosphomolybdic acid reagent (Sigma-Aldrich Co.). Column chromatography was performed with silica gel 60 (230-400 mesh) from E. Merck. Dowex 50WX8-400 cation exchange resin ($H^+$) form) was first eluted with methanol, 1N hydrochloric acid and deionized water. The cation forms of the resin were prepared by eluting with a 1N solution of the appropriate base followed by deionized water. All reaction products were colorless solids unless otherwise noted. All melting points were determined with an Electrothermal digital melting point apparatus model IA9200 and are uncorrected.

Methods for Synthesis of trans-dihydronarciclasine (1a)

2,3,4,7-O-Tetraacetoxy-narciclasine (2b)—Compound 2b is produced as follows. To a stirred solution of narciclasine (1.00 g, 3.25 mmol) in pyridine (3 ml under nitrogen), add acetic anhydride (6 ml). Stir for 16 hours at room temperature, add ice (50 ml) to the mixture, and extract with dichloromethane (3×20 ml). The combined extract is dried over $MgSO_4$, filtered and evaporated in vacuo to afford 2,3,4,7-O-Tetraacetoxy-narciclasine (2b) as a light brown powder (1.4 g, 90% yield).

2,3,4,7-Tetraacetoxy-trans-dihydronarciclasine (1b)

Method 1 for producing 1b. To a solution of narciclasine tetraacetate (2b) (0.97 g, 20.42 mmol) in glacial acetic acid (120 ml), add 5% Pd/C catalyst (0.56 g, 26 mol %). Stir the mixture under an atmosphere of hydrogen at room temperature for 3 hours and then filter the solution, such as through fluted filter paper. Dry the filtrate over $MgSO_4$, again filter and evaporate in vacuo. Purify the residue by column chromatography on silica gel eluting with 0.5% methanol in dichloromethane to afford the product (1b) as a powder (0.290 g, 30%) along with the cis-dihydro-peracetate (3b) as a solid (0.60 g, 62%). Analysis of 1b by comparison of NMR data found it to be identical with an authentic sample. (Pettit G. R., et al., Antineoplastic 162. *Zephyranthes candida*. J. Nat. Prod. 53:176-178; 1990.)

Method 2 for producing 1b. To a solution of narciclasine tetraacetate (2b) (0.200 g, 0.42 mmol) in a 1:1 mixture of ethanol/dichloromethane was added 10% Pd/C catalyst (0.004 g, 0.042 mmol). The mixture was stirred under 1 atm. of hydrogen at room temperature for 4 hours. The reaction mixture was then filtered through a pad of silica and the solvent removed in vacuo. The residue was then purified by column chromatography (flash silica; eluant 45:55 n-hexane-EtOAc) to afford the trans-dihydro-peracetate (1b) as a solid (0.131 g, 65%), along with the cis-dihydro-peracetate (3b) as a solid (0.050 g, 25%).

Trans-Dihydronarciclasine (1a). Dissolve 2,3,4,7-O-tetraacetoxy-trans-dihydronarciclasine (1b) (0.512 g, 1.07 mmol) in methanol:water (9:1) (20 ml), and add dichloromethane (12 ml) to aid in solubility. Add Potassium carbonate (0.009 g, 0.06 mmol) and stir the reaction at room temperature for three days. TLC ($CH_2Cl_2$:$CH_3OH$ 4%) shows complete conversion to the product.

The reaction mixture is concentrated and the residue purified by column chromatography on silica gel to give ($CH_2Cl_2$:$CH_3OH$ 4%) (1a) as an amorphous solid (0.134 g, 40%); mp 260° C. (dec), 285° C. (melts).

3,4-isopropylidene-7-deoxynarciclasine (2e)—Initially, 7-deoxynarciclasine (2c) (0.205 g, 0.704 mmol) and TsOH (0.133 g, 0.704 mmol) are dissolved in DMF (10 ml) and 2',2'-dimethoxypropane (0.864 ml, 7.04 mmol) is added. The resulting solution is stirred for 16 hours and then poured into water (50 ml) and extracted with ethyl acetate (4×30 ml). The combined organic phase is dried ($MgSO_4$), filtered and concentrated in vacuo to yield a pale yellow solid which is separated by column chromatography (flash silica; eluant 3:7 n-hexane-EtOAc) to afford the product 2e as a solid (0.215 g, 92%); Recrystallized from methanol as needles.

2-[tert-Butyl-1,1-dimethylsilyl]oxy-3,4-isopropylidene-7-deoxy-narciclasine (2f)—To 3,4-isopropylidene-7-deoxynarciclasine (2e, 0.024 g, 0.0725 mmol) in DMF (3 ml) is added TBDMSCI (0.016 g, 0.109 mmol) and imidazole (0.007 g, 0.109 mmol). Stir the resulting solution for 5 hours and remove the DMF in vacuo to afford a pale yellow oil. The residue is separated by column chromatography (flash silica; eluant 3:2/n-hexane-EtOAc) to afford the silyl ether as a solid (0.028 g, 87%): m.p. 269° C.

2-[tert-Butyl-1,1-dimethylsilyl]oxy-3,4-isopropylidene-7-deoxy-trans-dihydro-narciclasine (1d)—To a solution of 2-[tert-Butyl-1,1-dimethylsilyl]oxy-3,4-isopropylidene-7-deoxy-narciclasine (2f, 0.050 g, 0.112 mmol), in a 1:1 mixture of ethanol and dichloromethane (8 ml) add 10% Pd/C (1.2 mg, 0.0112 mmol). Stir the resulting mixture was stirred under 1 atm. of hydrogen for 4 hours and then pass through a short column of silica gel, eluting with ethyl acetate. Remove solvent in vacuo to afford a solid. Separate the residue by column chromatography (gravity, silica gel; eluant 7:3/n-hexane EtOAc) to yield a solid (0.028 g, 56%): m.p. 181.5-182.5° C.

Also isolated was 2-[tert-Butyl-1,1-dimethylsilyl]oxy-3,4-isopropylidene-7-deoxy-cis-dihydro-narciclasine (3c) as a solid (0.013 g, 26%): m.p. 237.5-238.5° C.

The third minor component isolated was 2-[tert-Butyl-1,1-dimethylsilyl]oxy-3,4-isopropylidene-7-deoxy-iso-dihydro-narciclasine (4c) as a solid (0.005 g, 10%): m.p. 246.5-248.0° C.

7-deoxy-trans-dihydronarciclasine (1c). 2-[tert-Butyl-1,1-dimethylsilyl]oxy-3,4-isopropylidene-7-deoxy-trans-dihydro-narciclasine (0.02 g, 0.045 mmol) is dissolved in tetrahydrofuran (2 ml) and formic acid (60%) (2 ml) is added at room temperature. The reaction mixture is heated to 60° C. for three hours. TLC (ethylacetate 15%:hexane) shows complete conversion to a slower moving product. The reaction is concentrated to a white residue which is purified by silica gel flash column chromatography ($CH_2Cl_2$:$CH_3OH$ 10%) to yield a white solid (13.1 mg, 71.4%) mp 230° C. $^1H$ NMR (300 MHz, DMSO-$d_6$) showed the silyl ether still present, which was confirmed by HRMS, APCI$^+$ calcd. for $C_{20}H_{30}NO_6Si$ (M+H)$^+$=408.1842, found m/z=408.1845. This material is taken without further purification to the silyl ether deprotection step.

2-[tert-Butyl-1,1-dimethylsilyl]oxy-7-deoxy-trans-dihydronarciclasine (0.037 g, 0.09 mmol) is dissolved in tetrahydrofuran (5 ml), and tetrabutylammoniumfluoride (TBAF) (0.01 ml, 0.01 mmol) is added and the reaction stirred at room temperature under argon. TLC($CH3_3OH$ 10%; $CH_2Cl_2$) after 6 hours shows incomplete conversion starting material to product, and therefore TBAF (0.1 ml, 0.1 mmol) is added and the reaction continued for 24 hours. Additional TBAF (0.1 ml, 0.1 mmol) was added after 24 hours. The reaction is stirred for 5 days. Ethyl acetate (35 ml) is added and the organic phase washed with brine (25 ml), dried $MgSO_4$, filtered and concentrated in vacuo to a yellow oil. The oil is taken up in tetrahydrofuran and eluted on a column of silica gel with a gradient elution using $CH_2Cl_2$:$CH_3OH$ 10%-$CH_2Cl_2$:$CH_3OH$ 30%. The product is isolated as a white solid, 13.4 mg, 50% and was identical by $^1H$ NMR with a natural sample of 7-deoxy-trans-dihydronarciclasine. (Gabrielsen, B., et al., Antiviral (RNA) activity of selected Amaryllidaceae isoquinoline constituents and synthesis of related substances. J. Nat. Prod. 55:1569-1581; 1992.)

Functional groups such as hydroxyl, ester and amide often direct the stereochemistry of hydrogenation. Homogenous hydrogenation of allylic alcohols usually occurs with high stereoselectivity. Catalysts used in such hydroxy-directed hydrogenation often include Wilkinson's catalyst (6) [RhCl(PPh$_3$)$_3$] and Crabtree's catalyst (7) [Ir(COD)(Pcy$_3$)(py)]PF$_6$ (8). Consequently, narciclasine, protected as its acetonide (2d), was treated with Crabtree's catalyst (7) in dichloromethane, but failed to yield any hydrogenation product. (Mondon, A., et al., Zur Kenntnis des Narciclasins. Chem. Ber. 108:445-463; 1975.) The reaction was also attempted with Wilkinson's catalyst (6) in toluene and again narciclasine acetonide (2d) resisted hydrogenation. With a related trisubstituted styrene that proved unreactive towards hydrogenation with Wilkinson's catalyst (6) even under forcing conditions, it was successfully hydrogenated when first converted to its alkoxide. That led exclusively to the cis isomer. (Thompson, H. W., et al., Stereochemical control of reductions. IV. Control of hydrogenation stereochemistry by intramolecular anionic coordination to homogeneous catalysts. J. Amer. Chem. Soc. 96:6232-6233; 1974.) This approach was unsuccessful when using narciclasine acetonide (2d). Without intending to be bound by this theory, because this reaction is believed to be associated with the olefin's ability to donate unshared electron pairs to unfilled surface orbitals of the catalyst metal, the double bond in narciclasine is probably too hindered to allow this type of hydroxy-directed hydrogenation. (Thompson, H. W. Stereochemical control of reductions. The directive effect of carbomethoxy vs. hydroxymethyl groups in catalytic hydrogenation. J. Org. Chem. 36:2577-2581; 1971.) So, attention was next directed to ionic hydrogenation. Interestingly, in our experiments narciclasine (2a) and derivatives (2b) and (2d) resisted hydrogenation with triethylsilane/trifluoroacetic acid in dichloromethane at −75° C. and at 25° C.

Hydrogentation of narciclasine (2a) using Adam's catalyst in ethanol results in the following: 28% of the trans isomer (1a) was usually obtained, along with 58% of the cis isomer 3a and 13% of iso-narciclasine (4a). (Mondon, A., et al., Zur Kenntnis des Narciclasins. Chem. Ber. 108:445-463; 1975.) The hydrogenation of narciclasine peracetate (2b) was conducted in the presence of 5% Pd/C (20 mol %) at 1 atm and a variety of solvents: ethyl acetate, ethanol, acetic acid, hexane, tetrahydrofuran, pyridine and dimethylformamide. (Thompson, H. W., et al., Stereochemical control of reductions. 5. Effects of electron density and solvent on group haptophilicity. J. Org. Chem. 41:2903-2906; 1976.), (Okamoto, T., et al., Lycoricidinol and lycoricidine. New plant growth regulators in the bulbs of Lycoris radiata Herb. Chem. Pharm. Bull. 16:1860-1864; 1968.), (Immirzi, A., et al., The crystal and molecular structure of narciclasine tetra-acetate. J. Amer. Chem. Soc. 240-240; 1972.) The results are shown in Table I.

TABLE I

Effect of solvent on hydrogenation of narciclasine acetate (2b) with 5% Pd/C (20 mol %) at 1 atm., 25° C. for 2 hours.

| | | Products | | | |
|---|---|---|---|---|---|
| Solvent | Wt. g Sm 2b | % Sm[a] 2b | % trans[a] 1b | % cis[a] 3b | % iso[a] 4b |
| hexane | 0.026 | 100 | — | — | — |
| pyridine | 0.022 | 100 | — | — | — |
| tetrahydrofuran | 0.025 | 70 | 15 | 15 | — |
| ethyl acetate | 0.025 | — | 47 | 40 | 13 |
| ethanol | 0.219 | — | 36 | 54 | 10 |
| ethanol:DCM (1:1) | 0.025 | 22 | 25 | 53 | — |
| ethanol:DCM (1:1)* | 0.200 | — | 65 | 25 | — |
| acetic acid | 0.024 | — | 51[b] | 47 | 2 |
| Dimethylformamide | 0.019 | — | 38 | 42 | 20 |

[a]Values determined by $^1$H NMR;
[b]Increased to 57% with 55 mol % of Pd/C, but dropped to 49% with 100 mol % of Pd/C.
*Isolated yield from reaction with 10% Pd/C (10% mol).

The trans:cis:iso ratios were determined by $^1$H-NMR and were based on a 100% conversion of starting material to product. The best ratio observed was 51:47:2 respectively with acetic acid as the solvent and the reaction carried out on a small scale (approx. 0.020 g of narciclasine peracetate). Scaleup of this reaction showed a wide variation in results. When 5 g of narciclasine was hydrogenated in acetic acid in the presence of 5% Pd/C (8 mol %) for 20 hr only starting material was recovered. When the hydrogenation was carried out on narciclasine peracetate 1 g using 10% Pd/C (25.8 mol %) the trans and cis products were isolated in 30% and 62% yield respectively following chromatography on silica gel. The solvent system dichloromethane:ethanol (1:1) gave good results when narciclasine tetraacetate (2b) (200 mg) was hydrogenated in the presence of 10% Pd/C (10 mol %). The yield of trans was 65% following chromatography. The peracetylated isomers (1b), (3b), and (4b) were separated by column chromatography on silica gel. The structure of the synthetic trans isomer (1b) was established by detailed spectral data comparison with an authentic sample. (Pettit G. R., et al., Antineoplastic 162. Zephyranthes candida. J. Nat. Prod. 53:176-178; 1990.)

Method for Synthesis of
7-deoxy-trans-dihydronarciclasine (1c)

Having developed a method for the hydrogenation of 2b to 1b, a similar method was sought for the interconversion of 7-deoxynarciclasine (2c) to 7-deoxy-trans-dihydronarciclasine (1c). This was achieved by initially protecting the cis diol unit as its acetonide (2d) in good yield (92%). The remaining hydroxyl group was protected as its silyl ether (2f) to avoid the potential problems which had already been encountered when attempting the hydrogenation of narciclasine acetonide (2d). With the silyl ether in hand, the hydrogenation of the olefin was attempted using the conditions which had been most successful in the reduction of peracetate 2b to the trans-dihydroperacetate (1b). Hydrogenation with 10% Pd/C (10 mol %) at 1 atm in ethanol/dichloromethane (1:1) of (2f) (0.05 g) gave a separable mixture of trans:cis:iso in 56%:26%:10% yields, respectively. However, this reaction suffered upon scaleup and yields of trans were reduced to 27% when the reaction was carried out on a 2 g scale. The synthetic trans-isomer (1d) was obtained by deprotection of the acetonide using formic acid (60%) followed by deprotection of the silyl ether with TBAF to yield 1c which was found to be identical with an authentic sample of 7-deoxy-trans-dihydronarciclasine (1d). (Gabrielsen, B., et al., Antiviral (RNA) activity of selected Amaryllidaceae isoquinoline constituents and synthesis of related substances. J. Nat. Prod. 55:1569-1581; 1992.)

As described below, the synthesis of sodium narcistatin (11) was improved (88% overall yield) and the modified reaction sequence was utilized to synthesize sodium 7-deoxynarcistatin (8), sodium 7-deoxy-trans-dihydronarcistatin (9) and sodium trans-dihydro-narcistatin (10). The human cancer cell line inhibitory isocarbostyril precursors were isolated from the bulbs of Hymenocallis littoralis obtained by horticultural production or reduction of narciclasine (2a) from the same source. Solvents were distilled prior to use and pyridine was dried over potassium hydroxide and distilled. The three new 3,4-cyclic phosphate prodrugs (8, 9, and 10), whose synthesis is discussed in further detail below, are being evaluated for further development as anticancer drugs.

Method for Synthesis of Sodium Narcistatin (11). Synthesis of 3,4-cyclic phosphate 11 from narciclasine (2a) (0.113 g, 0.368 mmol) was carried out in pyridine (4 ml) using tetrabutylammonium dihydrogen phosphate (0.075 g, 0.22 mmol) and dicyclohexylcarbodiimide (0.4 g, 1.94 mmol), with additional amounts of tetrabutylammonium dihydrogen phosphate (0.185 g) and dicyclohexylcarbodiimide (0.4 g) added after about the first 24 hours stirring at about 80° C. The reaction is stirred for about 96 hours, cooled and filtered to remove precipitated dicyclohexylurea (DCU). Water (100 ml) is added and the mixture refiltered to remove any residual DCU. The mother liquor is concentrated to minimum volume.

The aqueous fraction is eluted through an ion exchange column (sodium form). The UV active fractions are combined and lypholized to yield the phosphate 11 as a cream solid (88% yield). Rather than eluting the aqueous fraction via a sodium form of an ion exchange column, another suitable salt form (such as potassium or lithium) could be used to produce a compound such as potassium narcistatin or lithium narcistatin.

Method for Synthesis of 3,4-cyclic phosphates sodium 7-deoxynarcistatin (8), sodium 7-deoxy-trans-dihydronarcistatin (9) and sodium trans-dihydronarcistatin (10)

The 7-deoxynarciclasine (2c) and 7-deoxy-trans-dihydronarciclasine (1c) mixture separated from *H. littoralis* was acetylated by dissolving in pyridine (20 mL) and adding acetic anhydride (20 mL, 2.4 equiv.) The mixture slowly becomes a solution with stirring overnight at room temperature, and TLC ($CH_2Cl_2$—$CH_3OH$, 2%) showed no starting material. Ice water (200 ml) is added to the reaction mixture with vigorous stirring. A cream colored precipitate develops and is collected following being stirred for two hours to provide 13.7 g. Thereafter, the peracetate mixture (acetylation product) is separated by elution using 7:3 toluene-ethyl acetate, via silica gel column chromatography, to yield the following isocarbostyrils 12 (60% recovery) and 13 (19% recovery). Both 2,3,4-triacetoxy-7-deoxynarciclasine (12) and 2,3,4-triacetoxy-7-deoxy-trans-dihydronarciclasine (13) were then deprotected with potassium carbonate in aqueous methanol to afford the corresponding triols 14 and 15 in 72% yields.

The 3,4-cyclic phosphates 8, 9 and 10 were synthesized employing an improvement in the procedure we developed for synthesis of sodium narcistatin (11) using tetrabutylammonium dihydrogen phosphate and an excess of dicyclocarbodiimide in dry pyridine under argon at 80° C. for 48 hours. (Mondon, A., et al., *Chem. Ber.* 1975, 94, 617.), (Pettit, G. R., et al., *J. Nat. Prod.* 1986, 49, 995-1002.), (Pettit, G. R., et al., *J. Nat. Prod.* 2003, 66, 92-96.)

In each case, $^1$H-NMR of the crude product showed the reaction to be only 50% complete following a 24 hour period. Additional reagents were added at this stage and the reaction allowed to proceed to completion (a further 24 hours). Increasing the amount of tetrabutylammonium dihydrogen phosphate from 0.65 equivalents to 1 equivalent in the first 24 hours did not increase the reaction rate. Water was added to the reaction mixture to precipitate the dicyclohexylurea (DCU) and the pyridine/water filtrate was concentrated to remove the pyridine. An aqueous extract of the residue was passed through a Dowex 50WX8-400 ion exchange column (sodium form). The UV responsive fractions were combined and lyophilized to afford the new 3,4-cyclic phosphates designated sodium 7-deoxy-narcistatin (8, 88% yield), sodium 7-deoxy-trans-dihydro-narcistatin (9, 65% yield) and sodium trans-dihydro-narcistatin (10, 94% yield).

In a more preferred embodiment, deletion of the p-toluene sulfonic acid component increased the yield of phosphate 11 to 88% versus the original 50%. That was one of the major improvements that allowed new phosphates 8, 9 and 10 to be obtained in very good yields.

The cyclic phosphate prodrugs, along with the parent compounds were evaluated against a minipanel of human cancer cell lines and murine P388 lymphocytic leukemia. See Table 2.

TABLE 2

Aqueous Solubility, Human Cancer Cell Line and Murine P-388 Lymphocytic Inhibitory Activities

| Isocarbostyril | Aqueous Solubility 25° C. (mg/ml) | $ED_{50}$ (µg/ml) Leukemia P388 | $GI_{50}$ (µg/ml) | | | | | |
|---|---|---|---|---|---|---|---|---|
| | | | Pancreas-a BXPC-3 | Breast MCF-7 | CNS SF268 | Lung-NSC NCI-H460 | Colon KM20L2 | Prostate DU-145 |
| 2c | <1 | 0.019 | 0.070 | 0.046 | 0.120 | 0.053 | 0.084 | 0.051 |
| 1c | <1 | 0.029 | 0.046 | 0.034 | 0.059 | 0.043 | 0.051 | 0.040 |
| 1a | <1 | 0.0024 | 0.012 | 0.0053 | 0.020 | 0.0092 | 0.015 | 0.0066 |
| 10 | >190 | 1.7 | 5.3 | 4.0 | 6.3 | 4.7 | 5.6 | 3.9 |
| 10a | >10 | 0.42 | >1 | >1 | >1 | >1 | >1 | >1 |
| 10b | >10 | 1.4 | >1 | >1 | >1 | >1 | >1 | >1 |
| 11 | >10 | 1.6 | >10 | 7.2 | >10 | >10 | >10 | >10 |
| 11a | >5 | 0.39 | >1 | >1 | >1 | >1 | >1 | >1 |
| 11b | >5 | 1.7 | >1 | >1 | >1 | >1 | >1 | >1 |
| 12 | >10 | 0.88 | 5.6 | 4.6 | 8.8 | 7.8 | 9.6 | 5.2 |
| 12a | >1 | 0.26 | >1 | >1 | >1 | >1 | >1 | >1 |
| 12b | >1 | 0.35 | >1 | 0.64 | >1 | >1 | >1 | 0.54 |

Results of the cancer cell line evaluations reconfirmed the strong cancer cell growth inhibitory activity of 7-deoxy-trans-dihydronarciclasine (1c) and trans-dihydronarciclasine (1a). The corresponding 3,5-cyclic phosphates were less inhibitory under the experimental conditions employed. However, cleavage of the phosphate groups is expected to be very effective in vivo and such anticancer evaluations are now underway as part of the further preclinical development of these new anticancer drug candidates. (Pettit, G. R., et al., *J. Nat. Prod.* 2003, 66, 92-96.), (Dowlati, A., et al., *Cancer Research* 2002, 62, 3408-3416.), (Dziba, J. M., et al., *Thyroid* 2002, 12, 1063-1070.), (Eikesdal, H. P., et al., *Cancer Lett.* 2002, 178, 209-217.), (Prise, V., et al., *Int. J. Oncology* 2002, 21, 717-726.), (Hill, S. A., et al., *Int. J. Cancer* 2002, 102, 70-74.)

7-Deoxy-narciclasine (2c). To obtain 7-deoxy-narciclasine (2c), a solution of 2,3,4-triacetoxy-7-deoxy-narciclasine (12, 4.36 g) in $CH_3OH$—(99 ml) $H_2O$—(1 ml) $CH_3OH$ (30 ml) is added potassium carbonate (0.124 g), with stirring continued for 16 hours at room temperature while a white precipitate separated. The mixture is neutralized with acetic acid (2 ml), stirred for 15 minutes and concentrated to minimum volume. The colorless product is collected (2.18 g, 72%), recrystallization from acetic acid-methanol afforded fine needles: mp 205-210° C. (dec).

Sodium 7-Deoxy-narcistatin (8). A solution of 7-deoxy-narciclasine (2c, 0.2 g, 0.69 mmol) in pyridine (8 ml) was heated to 80° C. and tetrabutylammonium dihydrogen phosphate (0.15 g, 0.45 mmol, 0.65 equiv) followed by dicyclohexylcarbodiimide (0.8 g, 5.6 equiv) were added. The reaction was allowed to proceed at 80° C. for 24 hours. An $^1$H No analysis of the reaction mixture composition indicated a 50:50 mixture of starting material to product. Tetrabutylammonium dihydrogen phosphate (0.15 g) was added followed by DCCI (0.8 g) and the reaction continued for a further 24 hours. At this point, $^1$H NMR analysis of a sample from the reaction mixture showed reaction was complete. The reaction mixture was cooled and water (100 ml) was added. The precipitated dicyclohexylurea (DCU) was collected and the pyridine-water mother liquor was concentrated to minimum volume. The aqueous fraction was then passed through an ion exchange column (DOWEX 50W8-400) in the sodium form. The UV responsive fractions were combined and lyphollized to yield phosphate 8 as a colorless solid: 227 mg (88%); mp 255° C. (dec.).

Methods for Synthesis of 7-Deoxy-narcistatin prodrugs 8a and 8b

Sodium 7-deoxy-narcistatin (8, 52 mg) is dissolved in water (1 ml) and the solution is passed through a column of Dowex 50WX8-400, bearing the respective cation. For example, a column containing lithium or potassium cations, respectfully, may be used. The UV-active fractions are then combined and freeze-dried to give the corresponding narcistatin salt as a white solid, as follows:

Lithium 7-Deoxy-narcistatin (10a). 34 mg, mp 250° C. (dec).

Potassium 7-Deoxy-narcistatin (10b). 43 mg, mp 230-235° C. (dec).

7-Deoxy-trans-dihydro-narciclasine (1c). This compound is produced as follows. 2,3,4-triacetoxy-7-deoxy-trans-dihydro narciclasine (13, 0.14 g) is saponified in 9:1 aqueous methanol and with potassium carbonate (0.003 g), and is conducted as described above for obtaining alcohol 2c to yield triol 1e as a colorless solid; 89 mg (91% yield); mp>300° C. (dec.).

Sodium 7-Deoxy-trans-dihydro-narcistatin (9). The conversion of 7-deoxy-trans-dihydro-narciclasine (1c, 0.15 g, 0.51 mmol) to narcistatin 9 in pyridine (6 ml) with tetrabutylammonium dihydrogen phosphate (0.21 g, 0.62 mmol, 1.2 equiv), and dicyclohexylcarbodiimide (0.54 g, 2.62 mmol, 5.13 equiv) is conducted and the phosphate isolated as summarized for synthesis of narcistatin 8 (cf, above) including the additional tetrabutylammonium dihydrogen phosphate (0.21 g, 1.2 equiv) and DCCI (0.54 g). The aqueous extract of product is subjected to ion exchange column of Dowex 50WX8-400 (sodium form) and the UV fluorescing fractions combined and lyophilized as noted above (cf, 8). A solution of the sodium salt is prepared in methanol (15 ml with heating), the insoluble material is collected, and the filtrate concentrated to yield (0.124 g, 65%); mp 297° C. (dec.)

Method for Synthesis of 7-Deoxy-trans-dihydro-narcistatin prodrugs 11a and 11b

Sodium 7-deoxy-trans-dihydro-narcistatin (9, 30 mg) was dissolved in water (1 ml) and the solution passed through a column of Dowex 50WX8-400, bearing the respective cation. The UV-active fractions were combined and freeze-dried to give the corresponding narcistatin salt as a white solid.

Lithium 7-deoxy-trans-dihydro-narcistatin (9a). 25.4 mg, mp 253° C. (dec).

Potassium 7-deoxy-trans-dihydro-narcistatin (9b). 23.2 mg, mp 287° C. (dec).

Sodium trans-dihydro-narcistatin (10). Synthesis of 3,4-cyclic-phosphate 10 from trans-dihydronarciclasine (1a, 57 mg, 0.184 mmol) is accomplished in pyridine (2 ml) employing tetrabutylammonium dihydrogen phosphate (60 mg, 0.176 mmol and 60 mg for the delayed addition) and dicyclohexylcarbodiimide (0.18 g, 0.87 mmol) and 0.18 g for the second addition as described for preparation of phosphate 9 (refer above). (Trans-dihydro-narciclasine was synthesized by our group in 1992 from narciclasine according to procedures described by Mondon and Krohn. 19), (Mondon, A., et al., Chem. Ber., 1975, 108, 445-463.) The aqueous fraction eluted from the ion exchange column (Dowex 50WX8-400, sodium form) provided sodium trans-dihydro narcistatin (10) as a colorless solid (86 mg, 94% yield), mp>300° C.

Method for Synthesis of trans-dihydro-narcistatin prodrugs 10a and 10b

Sodium trans-dihydro-narcistatin (10, 0.010 g) was dissolved in water (1 ml) and the solution passed through a column of Dowex 50WX8-200, bearing the respective cation. The UV-active fractions are then combined and freeze-dried to give the corresponding trans-dihydro-narcistatin salt as a white solid.

Lithium trans-dihydro-narcistatin (10a). 8 mg, mp 275° C. (dec).

Potassium trans-dihydro-narcistatin (10b). 7.1 mg, mp 230-235° C. (dec).

What is claimed is:

1. A compound having the following structure:

$X = Na^+$

2. A compound having the following structure:

$X = Na^+$

3. A compound having the following structure:

X = Na⁺

4. A method for synthesizing trans-dihydronarciclasine, comprising the following steps:
   a) reacting narciclasine in acetic anhydride and pyridine to produce 2,3,4,7-O-tetraacetoxy-narciclasine;
   b) reacting the 2,3,4,7-O-tetraacetoxy-narciclasine with glacial acetic acid and palladium catalyst;
   c) filtering the product of step b) to produce a filtrate comprising 2,3,4,7-O-tetraacetoxy-trans-dihydronarciclasine and 2,3,4,7-O-tetraacetoxy-cis-dihydronarciclasine;
   d) drying the filtrate;
   e) purify the filtrate via column chromatography;
   f) dissolve the 2,3,4,7-O-tetraacetoxy-trans-dihydronarciclasine obtained from step e) in methanol and water and add potassium carbonate to product a reaction mixture;
   g) concentrate the reaction mixture of step f) and purify via column chromatography, thereby obtaining trans-dihydronarciclasine.

5. A method for synthesizing trans-dihydronarciclasine, comprising the following steps:
   a) reacting narciclasine in acetic anhydride and pyridine to produce 2,3,4,7-O-tetraacetoxy-narciclasine;
   b) reacting the 2,3,4,7-O-tetraacetoxy-narciclasine in a mixture of ethanol/dichloromethane and palladium catalyst;
   c) filtering the product of step b) to produce a filtrate comprising 2,3,4,7-O-tetraacetoxy-trans-dihydronarciclasine and 2,3,4,7-O-tetraacetoxy-cis-dihydronarciclasine;
   d) drying the filtrate;
   e) purify the filtrate via column chromatography;
   f) dissolve the 2,3,4,7-O-tetraacetoxy-trans-dihydronarciclasine obtained from step e) in methanol and water and add potassium carbonate to product a reaction mixture;
   g) concentrate the reaction mixture of step f) and purify via column chromatography, thereby obtaining trans-dihydronarciclasine.

6. A method for synthesizing 7-deoxy-trans-dihydronarciclasine, comprising the following steps:
   a) react 7-deoxynarciclasine and TsOH in DMF and 2',2'dimethoxypropane to form a first reaction mixture;
   b) stir the first reaction mixture;
   c) pour the first reaction solution into water and ethyl acetate to produce an organic phase and an aqueous phase;
   d) dry, filter, then concentrate the organic phase to produce 3,4-isopropyl idene-7-deoxy-narciclasine;
   e) react the 3,4-isopropylidene-7-deoxy-narciclasine with imidazole, and remove the DMF, thus producing 2-[tert-Butyl-1,1-dimethylsilyl]oxy-3,4-isopropyl idene-7-deoxy-narciclasine;
   f) react the 2-[tert-Butyl-1,1-dimethylsilyl]oxy-3,4-isopropylidene-7-deoxy-narciclasine in ethanol and dichloromethane with a palladium catalyst to form a second reaction mixture;
   g) stir the second reaction mixture, then pass the second reaction mixture through a silica gel column and elute with ethyl acetate to form a filtrate;
   h) remove the solvent from the filtrate to form a first solid;
   i) separate the first solid into its components using hexane/ethyl acetate in column chromatography, to yield (1) 2-[tert-Butyl-1,1-dimethylsilyl]oxy-3,4-isopropylidene-7-deoxy-trans-dihydronarciclasine, (2) 2-[tert-Butyl-1,1-dimethylsilyl]oxy-3,4-isopropylidene-7-deoxy-cis-dihydronarciclasine, and (3) 2-(tert-Butyl-1,1-dimethylsilyl]oxy-3,4-isopropylidene-7-deoxy-isodihydronarciclasine;
   j) react the 2-[tert-Butyl-1,1-dimethylsilyl]oxy-3,4-isopropylidene-7-deoxy-trans-dihydronarciclasine in tetrahydrofuran and formic acid with heating, to produce 7-deoxy-transdihydronarciclasine.

* * * * *